(12) United States Patent
Crockford et al.

(10) Patent No.: US 9,585,941 B2
(45) Date of Patent: Mar. 7, 2017

(54) EYE DROP FORMULATION

(71) Applicant: RegeneRX Biopharmaceuticals, Inc., Rockville, MD (US)

(72) Inventors: David Crockford, Newburyport, MA (US); Allan L. Goldstein, Washington, DC (US)

(73) Assignee: REGENERX BIOPHARMACEUTICALS, INC., Rockville, MD (US)

( * ) Notice: Subject to any disclaimer, the term of this patent is extended or adjusted under 35 U.S.C. 154(b) by 0 days.

(21) Appl. No.: 15/000,297

(22) Filed: Jan. 19, 2016

(65) Prior Publication Data

US 2016/0193301 A1 Jul. 7, 2016

Related U.S. Application Data

(62) Division of application No. 13/219,394, filed on Aug. 26, 2011, which is a division of application No. 11/917,848, filed as application No. PCT/US2006/023759 on Jun. 19, 2006, now Pat. No. 8,383,576.

(60) Provisional application No. 60/691,261, filed on Jun. 17, 2005, provisional application No. 60/776,947, filed on Feb. 28, 2006.

(51) Int. Cl.
| | |
|---|---|
| *A61K 9/08* | (2006.01) |
| *A61K 38/08* | (2006.01) |
| *A61K 38/22* | (2006.01) |
| *A61K 9/00* | (2006.01) |
| *A61K 47/18* | (2006.01) |
| *A61K 9/10* | (2006.01) |
| *A61K 9/14* | (2006.01) |

(52) U.S. Cl.
CPC ........ *A61K 38/2292* (2013.01); *A61K 9/0048* (2013.01); *A61K 9/08* (2013.01); *A61K 9/10* (2013.01); *A61K 9/14* (2013.01); *A61K 38/08* (2013.01); *A61K 47/186* (2013.01)

(58) Field of Classification Search
None
See application file for complete search history.

(56) References Cited

U.S. PATENT DOCUMENTS

| | | | |
|---|---|---|---|
| 4,444,757 A | 4/1984 | Strausser | |
| 5,342,620 A * | 8/1994 | Chowhan | A61K 9/0048 424/400 |
| 5,514,647 A | 5/1996 | Horowitz et al. | |
| 5,578,570 A * | 11/1996 | Goldstein | A61K 38/2292 514/1.4 |
| 5,593,964 A | 1/1997 | Goldstein et al. | |
| 7,268,118 B2 | 9/2007 | Kleinman et al. | |
| 2003/0072793 A1 | 4/2003 | Frey et al. | |
| 2004/0058875 A1 * | 3/2004 | Gamache | A61K 31/192 514/20.8 |
| 2004/0131626 A1 * | 7/2004 | Goldstein | A61K 38/2292 424/184.1 |
| 2004/0220111 A1 * | 11/2004 | Kleinman | A61K 38/1841 514/12.9 |

FOREIGN PATENT DOCUMENTS

| | | |
|---|---|---|
| EP | 0267015 A2 | 5/1988 |
| JP | 2005-506293 A | 3/2005 |
| WO | 9603158 A1 | 2/1996 |
| WO | 00/06190 A1 | 2/2000 |
| WO | 02/24234 A2 | 3/2002 |
| WO | 02/074193 A2 | 9/2002 |
| WO | 02750513 A2 | 9/2002 |
| WO | 2004/091550 A2 | 10/2004 |

OTHER PUBLICATIONS

Office Action issued in Chinese Patent Appln. No. 200680021662.0 on Jan. 5, 2013, along with English translation, 14 pages.
G. Sosne et al.: "Thymosin-B4 Inhibits Corneal Epithelial Cell Apoptosis after Ethanol Exposure In Vitro," Investigative Opthalmology & Visual Science, vol. 45, No. 4, Apr. 2004, pp. 1095-1100.
S. Yeh et al.: "Apoptosis of Ocular Surface Cells in Experimentally Induced Dry Eye," Investigative Opthalmology & Visual Science, vol. 44, No. 1, Jan. 2003, pp. 124-129.
Office Action issued in Indian Patent Appln. No. 255/KOLNP/2008 on Jan. 22, 2013, 2 pages.
P. Gonzalex et al.: "Genes Upregulated in theHuman Trabecular Meshwork in Response to Elevated Intraocular Pressure," Investigative Opthalmology & Visual Science, vol. 41, No. 2, Feb. 2000, pp. 352-361.
M. Schwartz: "Neurodegeneration and Neuroprotection in Glaucoma: Development of a Therapeutic Neuroprotective Vaccine," Investigative Opthalmology & Visual Science, vol. 44, No. 4, Apr. 2003, pp. 1407-1411.
Japanese Office Action issued in JP Application No. 2008-517207 mailed Oct. 25, 2011 along with English translation, 9 pages.
G. Sosne et al.: "Thymosin Beta 4 Promotes Corneal Wound Healing and Modulates Inflammatory Mediators in vivo," Exp. Eye Res., vol. 72, No. 5, 2001, pp. 605-608.
K. Mori: "Drug-Induced Corneal Epitheliopathy and Anti-Glaucoma Eyedrops," Atarashii-Ganka (Journal of the Eye), vol. 19, No. 11, 2002, pp. 1427-1431.
H. Ikeda et al.: "Pharmaceutical Properties of Ophthalmic Preparations Marketed as Over-the-Counter Drugs—Osmotic Ratio, pH, Total Number of Drops and Volume of a Drop-," Atarashii Ganka (Journal of the Eye), vol. 16, No. 2, 1999, pp. 249-252.
Australian Office Action issued in AU Application No. 2006261156 mailed Sep. 16, 2011, 3 pages.

* cited by examiner

*Primary Examiner* — James H Alstrum Acevedo
*Assistant Examiner* — Roy Teller
(74) *Attorney, Agent, or Firm* — Rothwell, Figg, Ernst & Manbeck, P.C.

(57) ABSTRACT

A composition with a polypeptide including amino acid sequence LKKTET or a conservative variant thereof, the composition further including a carrier for application to a surface of a body.

10 Claims, No Drawings

EYE DROP FORMULATION

CROSS-REFERENCE TO RELATED APPLICATION

The present application is a divisional of U.S. patent application Ser. No. 13/219,394, filed Aug. 26, 2011, which is a divisional of U.S. patent application Ser. No. 11/917,848, filed on Jul. 14, 2008, now U.S. Pat. No. 8,383,576, issued Feb. 26, 2013, which is a 35 U.S.C. §371 National Phase Entry Application from PCT/US2006/023759, filed on Jun. 19, 2006, and designating the United States, which claims the benefit of U.S. Provisional Application No. 60/691,261, filed Jun. 17, 2005 and U.S. Provisional Application No. 60/776,947, filed Feb. 28, 2006.

BACKGROUND OF THE INVENTION

Field of the Invention

The present invention relates to the field of LKKTET [SEQ ID NO:1] and/or LKKTNT [SEQ ID NO:2] compositions and methods.

Description of the Background Art

Thymosin beta 4 initially was identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

Many Tβ4 isoforms have been identified and have about 70%, or about 75%, or about 80% or more homology to the known amino add sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET [SEQ ID NO:1] or LKKTNT [SEQ ID NO:2], that appears to be involved in mediating actin sequestration or binding. Although not wishing to be bound by any particular theory, the activity of peptide agents as described herein may be due, at least in part, to the anti-inflammatory activity of such agents. Tβ4 also can modulate actin polymerization (e.g. β-thymosins appear to depolymerize F-actin by sequestering free G-actin). Tβ4'S ability to modulate actin polymerization may be due to its ability to bind to or sequester actin via the LKKTET [SEQ ID NO:1] or LKKTNT [SEQ ID NO:2] sequence.

There remains a need in the art for LKKTET [SEQ ID NO:1] and/or LKKTNT [SEQ ID NO:2] compositions and methods.

SUMMARY OF THE INVENTION

According to one embodiment, a composition comprising a peptide agent comprises amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, the composition including at least one amino acid stabilizing agent, the composition being in lyophilized form, or in a form capable of being lyophilized.

According to another embodiment, a composition comprising a peptide agent comprises amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, and at least one of a lyophilization bulking agent or an amino acid stabilizing agent, said composition being in lyophilized form.

DETAILED DESCRIPTION OF THE INVENTION

Many compositions that are administered to subjects for various purposes contain one or more ingredients that may cause injury to the subject.

For example, preservatives such as benzalkonium chloride (BAK), which are present in many ophthalmic and cosmetic products, may cause surface irritation and/or injury when the product is administered. Symptoms may include redness and discomfort.

There is a significant and growing problem with ocular surface irritation and apoptosis with chronic use of eye drops containing quaternary ammonium salts such as BAK. Patients often develop symptoms such as redness and general eye discomfort. A peptide agent in accordance with the present invention, such as thymosin beta 4 (Tβ4), can be utilized to treat or prevent damage or injury to eye tissue when administered to a subject in combination with contacting the eye tissue with a quaternary ammonium salt such as BAK.

Examples of quaternary ammonium salts to which the present invention may be applicable include BAK, cetrimide, benzoxonium chloride, and the like.

According to one embodiment, the peptide agent is administered together with the quaternary ammonium salt such as BAK as part of the same formulation, e.g., as an additive to a formulation containing BAK or other quaternary ammonium salt. Quaternary ammonium salts such as BAK are ingredients commonly used as preservatives in many ocular solutions, such as glaucoma eye drops.

In alternative embodiments, the peptide agent can be administered before administration of the quaternary ammonium salt such as BAK, and/or during administration of the quaternary ammonium salt such as BAK, and/or after administration of the quaternary ammonium salt such as BAK.

According to one embodiment the invention is particularly useful in preventing damage to corneal epithelial eye tissue, including prevention of apoptosis of cells of such eye tissue. For example, the invention may be utilized as an adjuvant for anti-glaucoma drops or other eye drops.

In accordance with one aspect, an ophthalmically acceptable composition comprises a peptide agent comprising amino acid sequence LKKTET [SEQ ID NO:1] or LKKTNT [SEQ ID NO:2], or a conservative variant thereof.

In accordance with another aspect, a method of treating eye tissue comprises topically administering to said eye tissue an ophthalmically acceptable composition comprising a peptide agent comprising amino acid sequence LKKTET [SEQ ID NO:1] or LKKTNT [SEQ ID NO:2], or a conservative variant thereof.

In one embodiment, the invention provides a method of treatment by contacting eye tissue with an effective amount of a composition which contains a peptide agent as described herein. Examples of direct administration include, for example, contacting the tissue, by direct application with a solution, lotion, salve, gel, cream, paste, spray, suspension, dispersion, hydrogel, ointment, oil or foam comprising a peptide agent as described herein.

Without being found to any specific theory, actin-sequestering peptides such as thymosin beta 4 (Tβ4 or TB4) and other agents including actin-sequestering peptides or peptide fragments containing amino acid sequence LKKTET [SEQ ID NO:1] or LKKTNT [SEQ ID NO:2] or conservative variants thereof, promote healthy eye tissue.

Thymosin beta 4 was initially identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

According to one embodiment the invention is preferably applicable to Thymosin β4, and/or Tβ4 isoforms, analogues or derivatives, including KLKKTET [SEQ ID NO:3], LKKTETQ [SEQ ID NO:4], oxidized Tβ4, Tβ4 sulfoxide, N-terminal variants of Tβ4 and C-terminal variants of Tβ4.

According to one embodiment, compositions which may be used in accordance with the present invention include peptide agents such as Thymosin β4 (Tβ4), and/or Tβ4 isoforms, analogues or derivatives, including oxidized forms of Tβ4 including Tβ4 sulfoxide, N-terminal variants of Tβ4, and C-terminal variants of Tβ4, and polypeptides or peptide fragments comprising or consisting essentially of the amino acid sequence LKKTET [SEQ ID NO:1] and conservative variants thereof. International Application Serial No. PCT/US99/17282, incorporated herein by reference, discloses isoforms of Tβ4 which may be useful in accordance with the present invention as well as amino acid sequence LKKTET [SEQ ID NO:1] or LKKTNT [SEQ ID NO:2] and conservative variants thereof, which may be utilized with the present invention. International Application Serial No. PCT/GB99/00833 (WO 99/49883), incorporated herein by reference, discloses oxidized Thymosin β4 which may be utilized in accordance with the present invention. Although the present invention is described primarily hereinafter with respect to Tβ4 and Tβ4 isoforms, it is to be understood that the following description is intended to be equally applicable to amino acid sequence LKKTET [SEQ ID NO:1] or LKKTNT [SEQ ID NO:2], peptides and fragments comprising or consisting essentially of LKKTET [SEQ ID NO:1] or LKKTNT [SEQ ID NO:2], conservative variants thereof and/or Tβ4 isoforms, analogues or derivatives, including oxidized Tβ4, N-terminal variants of Tβ4, and C-terminal variants of Tβ4.

According to one embodiment a composition in accordance with the present invention can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET [SEQ ID NO:1] or LKKTNT [SEQ ID NO:2], that appears to be involved in mediating actin sequestration or binding. Tβ4 has anti-inflammatory activity, and also can modulate actin polymerization (e.g. β-thymosins appear to depolymerize F-actin by sequestering free G-actin). Tβ4's ability to modulate actin polymerization may be due to its ability to bind to or sequester actin via the LKKTET [SEQ ID NO:1] or LKKTNT [SEQ ID NO:2] sequence. Thus, as with Tβ4, other proteins which are anti-inflammatory and/or bind or sequester actin, or modulate actin polymerization, including Tβ4 isoforms having the amino acid sequence LKKTET [SEQ ID NO:1], are likely to be effective, alone or in a combination with Tβ4, as set forth herein.

Thus, it is specifically contemplated that known Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such Tβ4 isoforms are useful in the methods of the invention, including the methods practiced in a subject. The invention therefore further provides compositions comprising Tβ4, as well as Tβ4 isoforms T1. A single unit dosage eye drop formulation comprising 0.1% to 0.6% by weight Tβ4 and an ophthalmically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET [SEQ ID NO:1] or LKKTNT [SEQ ID NO:2], for example, can similarly be employed in the methods of the invention. Such proteins may include gelsolin, vitamin D binding protein (DBP), profilin, cofilin, depactin, DnaseI, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, DnaseI, vilin, fragmin, severin, capping protein, β-actinin and acumentin as set forth herein. Thus, the invention includes the use of an polypeptide comprising the amino acid sequence LKKTET [SEQ ID NO:1] or LKKTNT [SEQ ID NO:2] and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

According to one embodiment, a composition in accordance with the present invention is an eye drop formulation.

According to one embodiment, a composition for use in the invention contains a peptide agent as described herein at a concentration within a range of from about 0.001-1000 micrograms per ml (mcg/ml), more preferably about 0.1-100 mcg/ml, most preferably about 1-10 mcg/ml. In particularly preferred embodiments, the peptide agent is Tβ4.

According to one embodiment the invention is useful for treating or preventing damage or injury to eye tissue resulting from contacting eye tissue with a quaternary ammonium salt such as BAK at concentrations within a range of about 0.0001-1% by weight, preferably within a range of about 0.001-0.1% by weight, and more preferably within a range of about 0.002-0.05% by weight. In one embodiment, the quaternary ammonium salt is at a concentration of about 0.005-0.02% by weight.

According to one embodiment the invention also includes a pharmaceutical composition comprising a peptide agent as described herein in an ophthalmically acceptable carrier. Such carriers include, e.g., those listed herein.

According to one embodiment the actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

According to one embodiment the methods and compositions using or containing a peptide agent as described herein may be formulated into compositions by admixture with ophthalmically acceptable non-toxic excipients or carriers.

According to one embodiment the topical formulation containing the active compound can also contain a physiologically compatible vehicle, as those skilled in the ophthalmic art can select using conventional criteria. The vehicles can be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

According to one embodiment an ophthalmic composition is advantageously applied topically to the eye, especially in the form of a solution, a suspension, an ointment, gel or foam.

According to one embodiment there are used for a corresponding ophthalmic composition customary pharmaceutically acceptable excipients and additives known to the person skilled in the art, for example those of the type mentioned below, especially carriers, stabilizers, solubilizers, tonicity enhancing agents, buffer substances, preservatives, thickeners, complexing agents and other excipients. Examples of such additives and excipients can be found in U.S. Pat. Nos. 5,134,124 and 4,906,613. Such compositions are prepared in a manner known per se, for example by mixing the active ingredient with the corresponding excipients and/or additives to form corresponding ophthalmic compositions. The active ingredient is preferably administered in the form of eye drops, the active ingredient being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic composition.

Carriers used in accordance with the present invention are typically suitable for topical or general administration, and are for example water, mixtures of water and water-miscible solvents, such as $C_1$-$C_7$-alkanols, vegetable oils or mineral oils comprising from 0.5 to 5% by weight hydroxyethylcellulose, ethyl oleate, carboxymethylcellulose, polyvinyl-pyrrolidone and other non-toxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof.

According to one embodiment the solubilizers used for an ophthalmic composition of the present invention are, for example, tyloxapol, fatty acid glycerol poly-lower alkylene glycol esters, fatty acid poly-lower alkylene glycol esters, polyethylene glycols, glycerol ethers or mixtures of those compounds. The amount added is typically sufficient to solubilize the active ingredient. For example, the concentration of the solubilizer is from 0.1 to 5000 times the concentration of the active ingredient. Lower alkylene means linear or branched alkylene with up to and including 7 C-atoms. Examples are methylene, ethylene, 1,3-propylene, 1,2-propylene, 1,5-pentylene, 2,5-hexylene or 1,7-heptylene. Lower alkylene is preferably linear or branched alkylene with up to and including 4 C-atoms.

Examples of buffer substances are acetate, ascorbate, borate, hydrogen carbonate/carbonate, citrate, gluconate, lactate, phosphate, propionate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 5 to 9, preferably from 6 to 8.2 and more preferably from 6.8 to 8.1.

Tonicity enhancing agents are, for example, ionic compounds, such as alkali metal or alkaline earth metal halides, such as, for example, $CaCl_2$, KBr, KCl, LiCl, NaBr, NaCl, or boric acid. Non-ionic tonicity enhancing agents are, for example, urea, glycerol, sorbitol, mannitol, propylene glycol, or dextrose. For example, sufficient tonicity enhancing agent is added to impart to the ready-for-use ophthalmic composition an osmolality of approximately from 50 to 1000 mOsmol, preferred from 100 to 400 mOsmol, more preferred from 200 to 400 mOsmol and even more preferred from 280 to 350 mOsmol.

Examples of preservatives are quaternary ammonium salts, such as cetrimide, benzalkonium chloride or benzoxonium chloride, alkyl-mercury salts of thiosalicylic acid, such as, for example, thimerosal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are cetrimide, benzalkonium chloride, benzoxonium chloride and parabens. Where appropriate, a sufficient amount of preservative is added to the ophthalmic composition to ensure protection against secondary contaminations during use caused by bacteria and fungi.

According to one embodiment the ophthalmic compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10 000. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxy-toluene or α-tocopherol acetate; stabilizers, such as a cyclodextrin, thiourea, thiosorbitol, sodium dioctyl sulfosuccinate or monothioglycerol; or other excipients, such as, for example, lauric acid sorbitol ester, triethanol amine oleate or palmitic acid ester. Preferred excipients are complexing agents, such as disodium-EDTA and stabilizers, such as a cyclodextrin. The amount and type of excipient added is in accordance with the particular requirements and is generally in the range of from approximately 0.0001 to approximately 90% by weight. A cyclodextrin is composed of several glucose units which have three free hydroxy groups per glucose. The amount of a cyclodextrin used in accordance with one embodiment may preferably range from 0.01-20% by weight, more preferably from 0.1-15% by weight and even more preferably from 1-10% by weight.

According to one embodiment the present invention relates also to an ophthalmic composition, which comprises a therapeutically effective amount of a peptide agent as described herein a carrier, a solubilizer and another therapeutically effective pharmaceutical agent which may be, for example, an antibiotic, an antiallergic, an anesthetic, another antiphlogistic, a corticosteroide, an agent suitable for lowering intra-ocular pressure, or another drug.

pH (Hydrogen Ion Concentration)

According to one embodiment, the pH of the inventive formulations should be as close to that of the tear film as possible. The physiologic pH of tears is approximately 7.4±0.2. Thus, from a comfort, tolerability and safety perspective, this would be the optimal pH of ophthalmic preparations.

Stimulation of tear secretion and eye blinking causes the pH to decrease in value. When the eyelid remains open for extended periods of time the tear-film is alkalized by equilibrium with the partial pressure of $CO_2$ in the surrounding air and a pH value of greater than 9 is attained. Both decreases and increases in pH occur without adverse consequences. Thus, there is some latitude in the pH range when formulating inventive formulations around pH of approximately 7.4.

Also, when a formulation is administered to the eye, it stimulates the flow of tears. Tear fluid is capable of quickly diluting and buffering small volumes of added substances, suggesting the eye can tolerate a fairly wide pH range offered by certain formulations.

Consequently, ophthalmic formulations may be within a range of from about pH 3.5 to 11.5. However, ophthalmic formulations may display pH ranges somewhat more narrowly from 3.5 to 9, preferably from 4.5 to 8 and most preferably from pH 5.5 to 7.8. The most preferred pH range is advantageous from the perspective solubility, chemical stability and therapeutic activity of the inventive compositions and a useful and relatively narrow range to prevent corneal damage.

Buffer Systems

According to one embodiment buffer systems are composed of a weak acid or base and its conjugate salt. The buffering capacity of the components in the system acts in such a way that, despite the addition of an acid or base and exposure to external influences of temperature, pressure, volume, redox potential, body fluids and tears, the pH will remain essentially constant. Although buffer capacity should be large enough to resist changes in the product pH (i.e., pH drift) for a reasonable shelf-life (i.e., under storage conditions), the buffer capacity of inventive ophthalmic formulations should be low enough to allow rapid readjustment of the product to physiologic pH upon administration to the eye. According to one embodiment buffer capacities for ophthalmic products should be within the range of 0.05 to 1.0. Preferred and most preferred buffer capacities range from 0.02 to 0.2 and 0.01 to 0.1, respectively for certain inventive compositions. Buffer capacity is determined by the following formula:

$$*\beta = \Delta B/\Delta pH$$

where β is buffer capacity, ΔB is the gram equivalent of strong acid/base to change pH of 1 liter of buffer solution and ΔpH is the change caused by the addition of strong acid/base.

According to one embodiment appropriate buffer systems may be sodium salts of the following acids: acetic; ascorbic; boric; carbonic; phosphoric; citric; gluconic; lactic; and propionic. Calcium salts of carbonic or propionic acid form appropriate buffer systems as do potassium salts of phosphoric acid. Tris buffer (tromethamine) is used intravenously as an alkalizer for the correction of metabolic acidosis and is one of the preferred buffers for use in this invention. Other preferred buffers are acetate, phosphate, citrate and borate. In certain instances a buffer system involving proton donor and proton acceptor groups of the amino acid residues of proteins may be preferable to the acid-base or an amine-base buffer.

The specific amount of a buffer substance used will vary and depends upon the amount that is deemed necessary to maintain a pH-environment suitable for the stability of inventive composition and to ensure and maintain a physiologically tolerable pH range.

Tonicity Agents

Of those listed herein the objective is to adjust the tonicity of the inventive ophthalmic compositions to that of natural tears to approximate physiological tonicity (e.g., 0.9% saline). For example, sodium chloride, potassium chlorides, calcium chloride, dextrose and/or mannitol may be added to the inventive peptide agent formulation. The amount of tonicity agent will vary, depending on the particular agent to be added. In general, certain inventive compositions will have a tonicity agent in an amount sufficient to cause the final composition to have an ophthalmically acceptable osmolality preferably 150-450 mOsm and most preferably 250-350 mOsm.

The preferred tonicity agents are sodium salts and potassium salts, particularly sodium and potassium chloride. The most preferred tonicity agent is sodium chloride.

Lubricants/Demulcent/Viscosity Enhancers

According to one embodiment compounds may be included which sooth the eye, reduce surface tension and improve wettability (contact) of an otherwise hydrophobic epithelial corneal surface, approximate the consistency of tears. Such compounds may also enhance the viscosity of the inventive compositions, allowing an inventive formulation to remain in the eye longer thus giving the peptide agent more time to exert its therapeutic activity or undergo absorption to reach the desired target.

Suitable viscosity enhancers in ophthalmic formulations and their concentration ranges used in certain inventive compositions include but are not limited to: (a) Monomeric polyols, such as tyloxapol (0.1-1%), glycerol (0.2-1%), propylene glycol (0.2 to 1%), ethylene glycol (0.2-1%); (b)

Polymeric polyols, such as polyethylene glycol (e.g., PEG 300, PEG 400)(0.2-1%); (c) Cellulose derivatives (polymers of the cellulose family), such as hydroxyethylcellulose (0.2-2.5%), hypromellose (0.2 to 2.5%), hydroxypropylmethyl cellulose (0.2-2.5%), methylcellulose (0.2-2.5%), carboxymethylcellulose sodium (0.2 to 2.5%), hydroxylpropylcellulose (0.2-2.5%); (d) Dextrans, such as dextran 70 (0.1% when used with another polymeric demulcent agent); (e) Water-soluble proteins such as gelatin (0.01%); (f) Vinyl polymers such as polyvinyl alcohol (0.1-4%), polyvinyl pyrollidine (0.1-4%); (g) Other polyols, such as polysorbate 80 (0.2-1%), povidone (0.1-2%); (h) Carbomers, such as carbomer 934P, carbomer 941, carbomer 940, and carbomer 974P, and (i) Polysaccharides/Glycosaminoglycans, such as hyaluronan (hyaluronic acid/hyaluronate) (0.1-3%), chondroitin sulfate (0.1-3%).

More than one viscosity enhancer may be added to an inventive composition to increase the viscosity of the carrier (vehicle). A preferred enhancer in the carrier of an inventive peptide agent formulation is carboxymethycellulose.

Viscosity

Viscosity describes a material's internal resistance to flow or change in form, when a stress is applied. The viscosity of a material (solution, semi-viscous gel, suspension, oleaginous ointments and ointment gels (viscous gels) is given in poise units. The unit, centipoise ("cp" or the plural "cps") is equal to 0.01 poise and is most often used in pharmaceutical applications. Compounds used to enhance viscosity are available in various grades such as 15 cps, 100 cps, etc., etc. The grade number refers to the viscosity which results when a fixed percentage aqueous solution of the enhancer is made. Generally, solutions are 1% or 2%; however, they can be as high as 4% with certain enhancers. Viscosity is measured at 20° or 25° C.

A suitable viscosity in an ophthalmic solution is between 25 and 50 centipoises (cps). The actual concentration of an enhancer required to produce that desired viscosity will depend on the grade of the enhancer. For example, if methycellulose 25 cps is used, a 1% solution will create a viscosity of 25 cps. If methycellulose 4000 cps is used, an 0.25% solution provides the desired viscosity. Standard references give tables of viscosities produced by percentage solutions and grades of ingredients.

According to one embodiment inventive formulations will exhibit a viscosity of >1 to 100,000 centipoises (cps) or greater. Inventive ointment compositions (oleaginous or viscous gels) may have viscosity grades that are greater than 100,000 cps. This is because ophthalmic ointments are intended to be thick when standing to prevent them from flowing away from the intended area of use. Following application and over time, temperatures within the conjunctival sac, or on the surface of the eye, where these ointments are deposited, will cause these ointments to "melt" and begin to flow.

The preferred viscosity ranges of various inventive formulation types are found in the table below:

| Formulation Type | Viscosity Range (cps) |
| --- | --- |
| Aqueous Solution | >1 to <1000 |
| Suspension | >1 to <1000 |
| Gel | >3 to 40,000 |
| Ointment, gel | >20,000 to 100,000 |
| Ointment, oleaginous | >20,000 to 100,000 |

Reducing Agents/Antioxidants/Oxygen-Sequestering Agents

Certain inventive compositions have the potential to be degraded by oxidation. Consequently, steps during the manufacture, control and packaging of an inventive composition may include protecting inventive compositions, susceptible to oxidation, by (1) displacing oxygen with nitrogen or a dense inert gas such as argon, (2) adding a reducing agent to minimize oxidative effects, (3) the introduction of a decoy molecule.

Common antioxidant (reducing) agents which may be used in ophthalmic formulations up to a concentration of 0.1% or more are sodium sulfite, sodium thiosulfite, sodium bisulfite, sodium metabisulfite, and thiourea. Sulfites can cause allergic-type reactions in certain people; consequently, patients receiving this type of antioxidant should be questioned about this potential reaction before being treated with an inventive composition containing the antioxidant. Other useful antioxidants compatible with the inventive compositions are ascorbic acid, EDTA/disodium edetate, acetic acid, citric acid, glutathione and acetylcysteine. These agents may also be regarded as stabilizers.

A decoy molecule or an oxygen sequestering protective agent may be added as stabilizers to an inventive formulation to minimize oxidative effects on the inventive formulation. The molecular decoy must have at least the same capability of being oxidized as the inventive formulation. One such decoy, for an inventive composition containing methionine is the amino acid, methionine, itself. Free methionine added to an inventive composition containing the amino acid methionine would compete for oxygen in the process of being oxidized to methionyl sulfoxide. A free oxygen-consuming agent is one that prevents other oxygen-reactive amino acids in the inventive composition/peptide from being oxidized. For the purposes of certain inventive compositions but not limited to such, a free oxygen-consuming agent is methionine.

Ophthalmic Ointments/Oleaginous Emollient Bases

Ophthalmic ointments tend to keep an active agent in contact with the eye longer than suspensions and certainly solutions. Most ointments, tend to blur vision, as they are not removed easily by the tear fluid. Thus, ointments are generally used at night as adjunctive therapy to eye drops used during the day.

Oleaginous ointment bases of inventive compositions are mixtures of mineral oil, petrolatum and lanolin all have a melting point close to body temperature. In the case of the inventive compounds, the compositions may include mineral oil, petrolatum or lanolin. According to one embodiment preferred compositions would include a combination of petrolatum, mineral oil and lanolin. The most preferred composition is an ointment combination containing white petrolatum, mineral oil and lanolin (anhydrous).

The peptide agent comprising amino acid sequence LKK-TET [SEQ ID NO:1] or LKKTNT [SEQ ID NO:2] or a conservative variant thereof is dissolved in a small amount of purified water or 0.9% saline to affect dissolution. This aqueous solution is incorporated into anhydrous lanolin and the then "liquid" lanolin (up to 10%) is mixed with the remaining ointment/oleaginous emollient base ingredients, mineral oil (up to 30%) and white petrolatum (up to 60%).

Ophthalmic ointment tubes are typically small holding approximately 1-5 grams of ointment, preferably 3.5 grams, and fitted with narrow gauge tips which permit the extrusion of narrow bands of ointment measured in inches or fractions thereof for dosing purposes.

Preservatives

Sterility is an absolute requirement of all ophthalmic formulations. Contaminated formulations may result in eye infections that could ultimately cause blindness, especially if the *P. aeruginosa* microbe is involved. Therefore, ophthalmic formulations as described herein must be prepared using techniques, unique for solutions, gels, suspensions and ointments of the inventive compositions that assure sterility. Sterile formulations must be packaged in sterile containers. Most topical ophthalmic products are typically packaged in multidose form. As such preservatives are required to prevent microbial contamination of an otherwise sterile product during use. Suitable preservatives include: Quaternary ammonium compounds (salts), such as benzalkonium chloride (0.001 to 0.02%), benzethonium chloride, cetalkonium chloride, cetrimide, benzododecinium bromide and benzoxonium chloride; Alkyl-mercury salts of thiosalicylic acid, such as thimerosal (0.001 to 0.005%); Parabens, such as methylparaben and propylparaben; Chelating agents, such as disodium edetate, sodium gluconate, sodium propionate; Other agents, such as chlorobutanol, boric acid, sorbic acid, phenylethanol (0.25%); Purite® chlorine dioxide; Polyquad® polyquaternium-1 (0.001%); and Aldox® myristamidopropyl diethylamine (0.005%); or other agents known to those skilled in the art.

Such preservatives are typically employed at a level of from 0.001% to 1.0% (w/v) to ensure protection against secondary microbial contaminations during use caused by bacteria, mold, and fungi.

Maximum concentrations of the following selected preservatives, presently approved for use in ophthalmic formulations, are shown in the table below:

| Agent | Maximum Concentration % |
| --- | --- |
| Benzalkonium chloride (BAK) | 0.01 |
| Benzethonium chloride | 0.01 |
| Clorobutanol | 0.5 |
| Phenylmercuric acetate | 0.004 |
| Phenylmercuric nitrate | 0.004 |
| Thimerosal (thiomersal) | 0.01 |
| Methyparaben | 0.2 |
| Propylparaben | 0.04 |

Source: FDA Advisory Panel on OTC Opthalmic Drug Products, Final report. December 1979

Selection of the appropriate preservative is based upon its anti-microbial effectiveness with the chosen inventive composition. Preferred preservatives for use in the inventive formulations are the combination of methylparaben (0.080%-0.1%) and propylparaben (0.016%-0.024%), benzalkonium chloride (BAK) (0.005%-0.02%, where 0.01% w/v is most preferred), a combination of BAK and EDTA (0.01-0.5%), which when used together have synergistic effects.

Unit dose compositions of the present invention will be sterile but unpreserved. Such compositions for the most part will not contain preservatives. Consequently, these compositions cannot be re-used and once-opened they must be discarded.

Bulking/Stabilizing Agents

Bulking/stabilizing agent(s) may be advantageous to maintain the hydration state of a lubricant, emollient or vehicle enhancer comprising an inventive composition during long-term storage. Associations appear to occur within or among polymer chains of these substances which after time favor the reduction of hydration state of these chains. These associations may be in the form of hydrogen bonds within and among the polymer chains which can manifest as a change in viscosity and texture of an ophthalmic formulation/composition in the present invention. Lyophilization bulking agents, which are principally sugars, may also be considered stress protectants, protecting compounds during the lyophilization cycle. Agents which greatly decelerate or eliminate this reduced state of hydration are a class of stabilizing or hydration-enhancing agents, the polyols at concentrations of 0.2 to 5% by weight. Representatives of such polyols are mannitol, sorbitol, glycerol, sucrose, related sugars, and the like. A most preferred stabilizing agent is the hydroscopic mannitol at concentrations ranging from 0.2% to 5% by weight.

Additionally, 50 mM amino acid stabilizers such as alanine (Ala), lysine (Lys), glycine (Gly) and glutamic acid (Glu) have been incorporated into the formulated peptide agent containing sequence LKKTET [SEQ ID NO:1] or LKKTNT [SEQ ID NO:2] or a conservative variant thereof to improve recovery from reconstituted aqueous solutions following lyophilization. The preferred amino acid stabilizers are arginine and glycine, while the most preferred 50 mM amino acid is glycine.

Inventive Peptide Administration

Exemplary Topical Delivery (for Surface-Acting Effects)

Peptide agents comprising amino acid sequences LKKTET [SEQ ID NO:1] or LKKTNT [SEQ ID NO:2] or a conservative variant thereof are administered to the surface of the eye for local effects to treat, for example:

1. Corneal epithelial wounds caused by but not limited to chemical burns, recurrent corneal erosions, epithelial debridement during surgery, corneal resurfacing procedures, Laser-assisted In Situ Keratornileusis (LASIK);
2. Corneal epithelial thinning caused by quaternary ammonium salts, such as BAK and the like;
3. Ocular inflammation (alone or in combination with corticosteroids) to treat, for example, conjunctivitis, blepharitis, keratitis, uveitis, scleritis, retinitis, optic neuritis, and temporal arteritis;
4. Microbial infection (alone or in combination with antibacterial, antifungal, or antiviral agents or in combination with both antimicrobials and anti-inflammatory agents);
5. Dry eye syndrome (xerophthalmia);
6. Red eye [alone or in combination with ocular decongestants (adrenergic vasoconstrictors of the conjunctiva), such as ephedrine, naphazoline, phenylephirine, tetrahydrozoline and antihistamines, such as pheniramine maleate) to whiten the eye];
7. Elevated intraocular pressure (IOP) and Glaucoma; and
8. Inflammatory or irritative conditions after traumatic injury or surgery or in various eye irritation disorders Topical inventive peptide agents are formulated as solutions, suspensions, gels and ointments. Inventive peptide agent formulations may be administered directly or indirectly by collagen sponges, inserts or the like. Every ophthalmic product, including topical ophthalmics, should be sterile in its final container to prevent microbial contamination of the eye. Preservatives are added to the formulation when packaged in a multidose container for more than one use to maintain sterility once the container has been opened. Ophthalmic formulations require that the pH, buffer capacity, viscosity and tonicity of the formulation are carefully controlled. Preferred pH ranges, buffers, viscosities and tonicities have been described herein.

Exemplary Formulation: Topical Solution for Eye Drops

Each milliliter of a topically-applied inventive peptide formulation contains the following peptide agent comprising amino acid sequence LKKTET [SEQ ID NO:1] or LKKTNT [SEQ ID NO:2] or a conservative variant as shown below.

Peptide at a concentration with a range of from about 0.001 to 1,000 mg/ml, preferably from about 0.01 mg/ml to 600 mg/ml, more preferably peptide at a concentration of about 0.1 mg/ml to 60 mg/ml, most preferably peptide at a concentration of about 1 mg/ml to 6 mg/ml.

Preferred Carrier/Vehicle: 20 mM Sodium citrate; 50 mM glycine; 3% sucrose; NaOH or HCl to adjust pH; Purified water, USP.

Exemplary Formulation: Topical Suspension for Eye Drops

With regard to ophthalmic suspensions containing a peptide agent comprising amino acid sequence LKKTET [SEQ ID NO:1] or LKKTNT [SEQ ID NO:2], particles must be less than 10 microns in size to minimize irritation to the eye. There may be a tendency of the solid undissolved particles to adhere to the conjunctiva. As drug is absorbed, these particles will dissolve to replenish the absorbed drug. This reservoir or depot effect increases the contact time and duration of action of a suspension compared to a solution.

Each milliliter of a topically-applied inventive peptide formulation contains the following peptide agent comprising amino acid sequence LKKTET [SEQ ID NO:1] or LKKTNT [SEQ ID NO:2] or a conservative variant as shown below:

Peptide at a concentration with a range of from about 0.001 to 1,000 mg/ml, preferably from about 0.01 mg/ml to 600 mg/ml, more preferably peptide at a concentration of about 0.1 mg/ml to 60 mg/ml, most preferably peptide at a concentration of about 1 mg/ml to 6 mg/ml.

Preferred Carrier/Vehicle: Peptide-encapsulation in poly (lactide-co-glycolide) PLGA microspheres; 20 mM Sodium citrate; 50 mM glycine; 3% sucrose; NaOH or HCl to adjust pH; Purified water, USP.

Exemplary Formulation: Topical Gel for Eye Drops

Each milliliter of a topically-applied inventive peptide formulation contains the following peptide agent comprising amino acid sequence LKKTET [SEQ ID NO:1] or LKKTNT [SEQ ID NO:2] or a conservative variant as shown below:

Peptide at a concentration of from about 0.001 to 1,000 mg/ml, preferably from about 0.01 mg/ml to 600 mg/ml, more preferably peptide at a concentration of about 0.1 mg/ml to 60 mg/ml, most preferably peptide at concentration of about 1 mg/ml to 6 mg/ml.

Preferred Carrier/Vehicle: carboxymethylcellulose sodium (0.5 to 1%); dibasic sodium phosphate; sodium chloride; propylene glycol; methylparaben; propylparaben; NaOH/HCl to adjust pH; Purified water, USP.

Exemplary Formulation: Topical Ointments

Each milliliter of a topically-applied inventive peptide formulation contains the following peptide agent comprising amino acid sequence LKKTET [SEQ ID NO:1] or LKKTNT [SEQ ID NO:2] or a conservative variant as shown below:

Peptide at a concentration of from about 0.001 to 1,000 mg/ml, preferably from about 0.01 mg/ml to 600 mg/ml, more preferably peptide at concentration of about 0.1 mg/ml to 60 mg/ml, most preferably peptide at concentration of about 1 mg/ml to 6 mg/ml.

Preferred Carrier/Vehicle (1): carboxymethycellulose sodium (2.5%); dibasic sodium phosphate; propylene glycol; methylparaben; propylparaben; sodium chloride; NaOH/HCl to adjust pH; purified water.

Preferred Carrier/Vehicle (2): "liquid" lanolin (10%); mineral oil (30%), and white petrolatum (60%).

Exemplary Topical Delivery for Steroid-Sparing Effects

Corticosteroids inhibit the inflammatory response to a variety of inciting agents.

Dexamethasone ophthalmic suspension (0.1%); Dexamethasone ophthalmic ointment (0.05%); and Dexamethasone Sodium Phosphate Ophthalmic Solution (0.1%)

Fluorometholone Ophthalmic Ointment (0.1%); Fluorometholone Ophthalmic Suspensions (0.25-1%); and Fluorometholone Acetate Ophthalmic Suspension (0.1%)

Lotoprednol etabonate (0.5%)

Medrysone Ophthalmic Suspension (1%)

Prednisolone Acetate Ophthalmic Suspensions (0.12-1%) and Prednisolone Sodium Phosphate Opthmalmic Solutions (0.125-1%)

Rimexolone Ophthalmic Suspension (1%)

These agents, however, can elevate intraocular pressure (IOP) and, in susceptible individuals, can induce glaucoma with damage to the optic nerve, defects in visual acuity and fields of vision, and posterior subcapsular cataract formation. Cataract formation is a complication more likely to occur with high-dose, longterm use. Some corticosteroids, such as fluorometholone acetate, medrysone, and loteprednol cause less elevation of IOP than others. Prolonged use may also suppress the host immune response and thus aid in the establishment of secondary ocular infections from fungi and viruses liberated from ocular tissue. Topical corticosteroids are known to delay or slow wound healing.

Administration of topically-applied eye drops or ointments containing an inventive peptide agent comprising amino acid sequence LKKTET [SEQ ID NO:1] or LKKTNT [SEQ ID NO:2] or a conservative variant to inhibit an inflammatory response to an inciting agent has the potential to be steroid-sparing.

Exemplary Intraocular Drug Delivery—Conjunctival/Sclera Instillation

The topical conjunctival route of entry plays an important role in the penetration of drugs into the anterior segment. Furthermore, topically applied drugs have been shown to have access to the sclera from the conjuctiva. The potential for transport or diffusion through the sclera lies in the large and accessible surface area of this tissue, with its high degree of hydration, hypocellularity, and permeability that do not decline significantly with age. As such, it is conceivable that inventive compositions could find their way to the posterior segment by this noninvasive route of administration. Data suggest that the sclera is readily permeable to even large molecular weight compounds (~150 kD), much larger than a peptide agent comprising amino acid sequence LKKTET [SEQ ID NO:1] or LKKTNT [SEQ ID NO:2] or a conservative variant thereof. The recent finding that topically-applied nepafenac inhibited choroidal and retinal neovascularization by decreasing the production of VEGF, and a large molecular weight peptide like insulin (5.8 kD) can accumulate in the retina and optic nerve after topical administration indicates that topically applied inventive compositions, all of which having molecular weights of <150 kD, could not only reach the posterior segment through conjunctival penetration, but that they can also be therapeutic. Topical solutions, suspensions, gels or ointments of peptide agents comprising amino acid sequences LKKTET [SEQ ID NO:1] or LKKTNT [SEQ ID NO:2] or conservative variants described above are suitable formulations for topical conjuctival and scleral application.

Additionally, subconjunctival administration by injection of inventive compositions of the peptide agent comprising amino acid sequence LKKTET [SEQ ID NO:1] or LKKTNT [SEQ ID NO:2] or a conservative variant thereof is useful in delivering anti-inflammatory and anti-microbial regimens, sensitive to the inventive composition, to treat serious ocular inflammation and ocular infections, such as uveitis and endophthalmitis, and glaucoma.

Preferred Injectable Formulation: Each ml of a peptide agent comprising amino acid sequence LKKTET [SEQ ID NO:1] or LKKTNT [SEQ ID NO:2] or a conservative variant contains:

Peptide at a concentration of from about 0.001 to 1,000 mg/ml, preferably from about 0.01 mg/ml to 600 mg/ml, more preferably peptide at a concentration of about 0.1 mg/ml to 60 mg/ml, most preferably peptide at a concentration of about 1 mg/ml to 6 mg/ml.

Preferred Carrier/Vehicle: 20 mM Sodium citrate; 50 mM glycine; 3% sucrose; NaOH or HCl to adjust pH; Water for Injection, USP.

Exemplary Intraocular Drug Delivery—Transcorneal Instillation

Topically applied drugs do penetrate into the intraocular environment through the hydrophobic cornea; however, transcorneal transport is not the most effective process as it is estimated that only one- to three-tenths of a dose penetrates into the eye while most of the drug remains confined to the superficial epithelium layer. Passive diffusion of inventive peptide compositions across the cornea is largely influenced by their solubility, molecular weight and degree of ionization. Having a net negative charge and a relatively high molecular weight, an inventive peptide agent, formulated as a topically-applied drug will find it difficult to penetrate the intact cornea. This is supported by the fact that pores, localized between epithelial cells in the cornea allow paracellular permeation of only small molecules of about 500-molecular weight or less. However, in cases where the intact corneal epithelium has been disrupted by erosion, for example, or exposed to a substance or penetrating agent that opens tight junctions between epithelial cells, inventive compositions will pass through the cornea into the intraocular space more efficiently.

Topical solutions, gels or ointments of peptide agents comprising amino acid sequences LKKTET [SEQ ID NO:1] or LKKTNT [SEQ ID NO:2] or conservative variants described above are suitable formulations for transcorneal instillation.

Exemplary Intraocular Drug Delivery—Periocular Injection

Periocular injection formulations of inventive peptide agents are used in cases where ocular inflammation is not responding to a topical eye drops alone and in inflammatory conditions such as anterior uveitis, posterior uveitis, endophthalmitis, and optic neuritis. The peptide agent is injected just below the conjunctiva or in the space below Tenon's capsule. Here, more absorption will occur and consequently, more drug will be available to the desired site. Periocular injection is additive to topical therapy but lacks the convenience and is not well-tolerated to be considered a first line treatment.

Preferred Injectable Formulation: Each ml of the peptide agent comprising amino acid sequence LKKTET [SEQ ID NO:1] or LKKTNT [SEQ ID NO:2] or a conservative variant contains:

Peptide at a concentration of from about 0.001 to 1,000 mg/ml, preferably from about 0.01 mg/ml to 600 mg/ml, more preferably peptide at a concentration of about 0.1 mg/ml to 60 mg/ml, most preferably peptide at a concentration of about 1 mg/ml to 6 mg/ml.

Preferred Carrier/Vehicle: 20 mM Sodium citrate; 50 mM glycine; 3% sucrose; NaOH or HCl to adjust pH; Water for Injection, USP.

Exemplary Intraocular Drug Delivery—IntraVitreal/IntraAqueous Administration

As an alternative to transcorneal, transconjuctival, and transscleral transport, delivery of inventive peptide agents to the intraocular tissues can be achieved by injection into the vitreous or aqueous cavity. The vitreous is made of a hydrogel (water, hyaluronic acid and collagen), which fills the cavity between the retina and the lens, while the aqueous is a watery fluid which fills the cavity between the lens and the iris. Intravitreal or intra-aqueous injections of an inventive peptide agent, formulated as a solution allows for immediate exposure of intraocular tissues to the peptide agent. To achieve a continuous intraocular presence of an inventive agent, which may be quickly eliminated from the vitreous, would require repeated injections that increase the risk of endophthalmitis, damage to lens, retinal detachment and may be poorly tolerated. To obviate this obstacle, the inventive peptide agent would be encapsulated within phospholipid membranes, i.e., liposomes, biodegradable microspheres, nanoparticles, or biodegradable lactone based polymers that includes polyesters made by polycondensation of L-lactide, glycolide, caprolactone, dioxanone, cyclic carbonates and their derivatives. Polylactide and polyglycolide, known also as poly(lactic-acid) PLA and poly(glycolic-acid) PGA, respectively, and particularly their co-polymers poly (lactide-co-glycolide) PLGA are the most investigated biodegradable polymers, which also can also be applied as carriers for the inventive peptide agents. Additionally, peptide-polymer conjugates such as the covalent linkage of the peptide agent comprising LKKTET [SEQ ID NO:1] or LKKTNT [SEQ ID NO:2] or a conservative variant thereof with synthetic and natural polymers such as polyethylene glycol (PEG) and dextran, including the cyclodextrans, allow for an improve pharmacokinetic profile, resulting in a decrease in inventive peptide clearance.

Intravitreal or intra-aqueous administration of an inventive peptide agent may be indicated in treatment of ocular inflammation, ocular infection (bacterial, fungal or viral) and the glaucomatous eye by controlling F-actin architecture in outflow pathway cells. (Read A T et al., Exp Eye Res, 2006 June:82(6):974-85).

A Preferred Injectable Formulation: Each ml of the peptide agent comprising amino acid sequence LKKTET [SEQ ID NO:1] or LKKTNT [SEQ ID NO:2] or a conservative variant contains:

Peptide at a concentration of from about 0.001 to 1,000 mg/ml, preferably from about 0.01 mg/ml to 600 mg/ml, more preferably peptide at a concentration of about 0.1 mg/ml to 60 mg/ml, most preferably peptide at a concentration of about 1 mg/ml to 6 mg/ml.

Preferred Carrier/Vehicle (1): 20 mM Sodium citrate; 50 mM glycine; 3% sucrose; NaOH or HCl to adjust pH; Water for Injection, USP.

Preferred Carrier/Vehicle (2): Peptide encapsulation in PLGA microspheres; 20 mM Sodium citrate; 50 mM glycine; 3% sucrose; NaOH or HCl to adjust pH; Water for Injection, USP.

Exemplary Formulation Dosing

Topical Solutions and Suspensions:

One drop per administration and at least five minutes between administrations is recommended. Immediately after instilling a drop on the eye, place pressure on the lacrimal sac for one or two minutes to reduce the rate of drug loss through this pathway. Injectable Dosing: Use 27-30 gauge needle, 0.5 inch length.

A composition according to one embodiment may be in lyophilized form, or in a form capable of being lyophilized, comprising a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, the composition further comprising at least one amino acid stabilizing agent. The composition may comprise a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, and at least one of a lyophilization bulking agent or an amino acid stabilizing agent, said composition being in lyophilized form. The composition may further comprise at least one of an acidic or basic pH adjusting agent capable of adjusting pH of the composition to a desired physiologically acceptable pH level in an aqueous medium, and a buffer to substantially maintain said desired pH in said aqueous medium. The amino acid stabilizing agent may comprise at least one of alanine, lysine, glycine or glutamic acid. The amino acid stabilizing agent may comprise at least one 50 mM amino acid stabilizer. The amino acid stabilizing agent may comprise 50 mM glycine. The composition may further comprise a bulking agent comprising at least one of carbohydrates, sugar alcohols, mono-, di-, and polysaccharides, polyols, mannitol, sorbitol, glycerol, sucrose or dextrose. The pH adjusting agent may include at least one of NaOH or HCl. The buffer may include at least one of a sodium salt of at least one of acetic, ascorbic, boric, carbonic, phosphoric, citric, gluconic, lactic or propionic acids, a calcium salt of carbonic or propionic acids, a potassium salt of phosphoric acid, Tris buffer, acetate, phosphate, citrate or borate buffers. The buffer may be sodium citrate. The buffer may have a buffer capacity of about 0.05-1.0. The buffer may have a buffer capacity of about 0.02-0.2, or about 0.01-0.1. The desired pH level may be within a range of about 3.5-11.5, about 3.5-9, about 4.5-8, or about 5.0-7.8. The desired pH level may be about 5.5. The peptide agent may comprise amino acid sequence KLKKTET [SEQ ID NO:3], amino acid sequence LKKTETQ [SEQ ID NO:4], Tβ4, an N-terminal variant of Tβ4, a C-terminal variant of Tβ4, or an isoform of Tβ4. The composition may further include an aqueous medium, wherein said peptide agent is present in said aqueous medium at a concentration within a range of about 0.001-1,000 mg/ml. The composition may further include at least one steroid.

A composition according to another embodiment is for administration to skin tissue of a subject, and comprises a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, in said tissue, the composition further comprising a quaternary ammonium salt and a topical carrier for application to skin tissue of said subject. The peptide agent may comprise amino acid sequence LKKTET [SEQ ID NO:1], amino acid sequence LKKTETQ [SEQ ID NO:4], Tβ4, an N-terminal variant of Tβ4, or an isoform of Tβ4. The quaternary ammonium salt may comprise benzalkonium chloride. The peptide agent may be at a concentration of about 0.001-1,000 mg/ml and said quaternary ammonium salt may be present in said composition at about 0.001-1% by weight. The composition may be in a form of a solution, gel, cream, paste, lotion, spray, suspension, dispersion, salve, hydrogel, ointment or foam formulation. The composition may be a cosmetic formulation.

A pharmaceutical or cosmetic combination according to another embodiment comprises a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, the combination further comprising a quaternary ammonium salt, wherein said agent and said salt can be administered to a subject separately or together. The peptide agent may comprise amino acid sequence LKKTET [SEQ ID NO:1], amino acid sequence LKKTETQ [SEQ ID NO:4], Tβ4, an N-terminal variant Tβ4, or an isoform of Tβ4. The quaternary ammonium salt may be benzalkonium chloride. The combination may comprise a pharmaceutical, ophthalmic or cosmetic composition comprising said peptide agent at a concentration of about 0.001-1,000 mg/ml, and wherein said quaternary ammonium salt may be present in said composition at about 0.0001-1% by weight. The combination may comprise an ophthalmic composition further comprising an opthalmically acceptable carrier. The composition may comprise an eye drop composition.

According to a further embodiment, method of treatment for treating, preventing, inhibiting or reducing tissue deterioration, injury or damage resulting from administration of a quaternary ammonium salt to a subject, comprises administering said quaternary ammonium salt to said subject, and administering to said subject a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof in said tissue. The agent may be administered to said subject prior to, concurrently with or after said administration of said quaternary ammonium salt. The agent and said salt may be administered together as a composition. The composition may further comprise an opthalmically acceptable carrier. The composition may comprise an eye drop composition. The composition may comprise a cosmetically acceptable carrier. The composition may be in a form of a solution, gel, cream, past, lotion, spray, suspension, dispersion, salve, hydrogel, ointment or foam formulation. The peptide agent may comprise amino acid sequence KLKKTET [SEQ ID NO:3], amino acid sequence LKKTETQ [SEQ ID NO:4], Tβ4, an N-terminal variant of Tβ4, a C-terminal variant of Tβ4, or an isoform of Tβ4. The quaternary ammonium salt may comprise benzalkonium chloride. The peptide agent may be included in said composition at a concentration within a range of about 0.001-1,000 mg/ml, and said quaternary ammonium salt may be present in said composition within a range of about 0.0001-1% by weight.

A composition according to still a further embodiment comprises a peptide agent comprising amino acid sequence LKKTET [SEQ ID NO:1] or LKKTNT [SEQ ID NO:2], a conservative variant thereof, or a stimulating agent that stimulates production of an LKKTET [SEQ ID NO:1] or LKKTNT [SEQ ID NO:2] peptide, or a conservative variant thereof, and an opthalmically acceptable carrier, an antimicrobially effective preservative, a tonicity agent for providing said composition with an opthalmically acceptable tonicity, a comfort enhancing agent, at least one of an acidic or basic pH adjusting agent capable of adjusting pH of the composition to a desired ophthalmically acceptable pH level, and a buffer to substantially maintain said desired pH level. The composition may further comprise at least one of an antioxidant or an oxygen sequestering agent. The antioxidant or oxygen sequestering agent may comprise at least one of sodium sulfite, sodium thiosulfite, sodium bisulfite, sodium metabisulfite, thiourea, ascorbic acid, EDTA/disodium edentate, acetic acid, citric acid, glutathione, acetylcysteine or methionine. The antioxidant or oxygen sequestering agent may be at a concentration in said composition within a range of about 0.0001-1.0% by weight. The antimicrobially effective preservative may comprise at least one of a quaternary ammonium compound, benzalkonium chloride, benzethonium chloride, cetalkonium chloride, cetrimide, benzododecinium bromide, benzoxonium chloride, an alkyl-mercury salt of thiosalicylic acid, thimerosal, phenylmercuric nitrate, phenylmercuric acetate, phenylmercuric borate, a paraben, methylparaben, propylparaben, a chelating agent, disodium edentate, sodium gluconate, sodium propionate, an alcohol, chlorobutanol, benzyl alcohol, phenyl ethanol, a guanidine derivative, chlorohexidine, polyhexamethylene biguanide, sorbic acid, boric acid, chlorine dioxide, polyquaternium or myristamidopropyl diethylamine. The preservative may be present in said composition at a concentration within a range of about 0.0001-5.0% (w/v). The composition may further include at least one opthalmically acceptable stabilizing agent. The stabilizing agent may comprise at least one of a polyol, mannitol, sorbitol, glycerol, sucrose, an amino acid stabilizer, alanine (Ala), lysine (Lys), glycine (Gly) or glutamic acid (Glu). The stabilizing agent may be present in said composition at a concentration within a range of about 0.01-10% by weight. The tonicity agent may comprise at least one of an ionic compound, alkali metal halide, alkaline earth metal halide, CaCl2, KBr, KCl, LiCl, NaBr, NaCl, boric acid, a non-ionic compound, urea, glycerol, sorbitol, mannitol, propylene glycol, or dextrose. The composition may have an osmolality within a range of about 50 to 1000 mOsmol. The adjusting agent may include at least one of NaOH or HCL. The buffer may include at least one of a sodium salt of acetic acid, a sodium salt of ascorbic acid, a sodium salt of boric acid, a sodium salt of carbonic acid, a sodium salt of phosphoric acid, a sodium salt of citric acid, a sodium salt of gluconic acid, a sodium salt of lactic acid, a sodium salt of propionic acid, a calcium salt of carbonic acid, a calcium salt of propionic acid, a potassium salt of phosphoric acid, Tris buffer, an acetate buffer, a phosphate buffer, a citrate buffer or a borate buffer. The desired pH level may be within a range of about 3.5-11.5. The buffer may have a buffer capacity of about 0.05-1.0. The peptide agent may comprise amino acid sequence KLKKTET [SEQ ID NO:3], amino acid sequence LKKTETQ [SEQ ID NO:4], T$\beta$4, an N-terminal variant of T$\beta$4, a C-terminal variant of T$\beta$4, or an isoform of T$\beta$4. The composition may further comprise an aqueous medium, wherein said peptide agent is present in said aqueous medium at a concentration within a range of about 0.001-1,000 mg/ml. The composition may be in a form of a solution, gel, cream, paste, lotion, spray, suspension, dispersion, salve, hydrogel, ointment or foam formulation. The composition may comprise an eye drop composition. The peptide agent may be present in said composition encapsulated with at least one of phospholipid membranes, liposomes, microspheres, nanoparticles or biodegradable polymers, or as a peptide-polymer conjugate.

Example

Thymosin beta 4 (T$\beta_4$), a 43 amino acid molecule, promotes ocular wound healing, decreases ocular inflammation, and has anti-apoptotic effects on corneal epithelium. In this study, the effect of T$\beta_4$ on the survival of cultured human corneal epithelial cells exposed to benzalkonium chloride (BAK) was measured.

Human corneal epithelial cells at approximately 80% confluence were treated with 0%, 0.001%, 0.01%, or 0.1% BAK for 15 minutes. After 3 and 24 hours of recovery in culture medium, cell proliferation was measured using a colorimetric BrdU incorporation assay. Apoptosis was measured using a colorimetric annexin-based cell death assay. Studies were repeated in the presence of 1 mcg/ml T$\beta_4$, an in vitro dosage demonstrated effective in several published studies. To further assess the ability of Tb$_4$ to prevent apoptosis, corneal epithelial cells were treated with 0.01% BAK±T$\beta_4$ over a 5 day time course.

At all BAK concentrations used, corneal epithelial cell proliferation was inhibited, and apoptosis was increased, compared to control at 3 and 24 hours recovery time. At the 3 and 24 hour time points, T$\beta_4$ did not abrogate the deleterious effects of BAK; cell proliferation was not promoted by T$\beta_4$ and apoptosis was not inhibited. However, at longer times in culture (2 to 5 days), T$\beta_4$ treatment significantly inhibited the BAK-initiated epithelial cell apoptosis. In addition, T$\beta_4$-treated cells demonstrated decreased apoptosis compared to those cultured in medium alone for 5 days.

BAK, a preservative used in many commercially available ocular solutions, induces corneal epithelial cell apoptosis in culture, suggesting that long-term exposure is deleterious to corneal health. The study reported here indicates that T$\beta_4$ is able to overcome the deleterious pro-apoptotic effects of BAK. Since many BAK-containing eye drops are typically used for extended periods of time, T$\beta_4$ is indicated to be a useful additive to solutions containing this preservative.

The invention claimed is:

1. A single unit dosage eye drop formulation comprising 0.1% to 0.6% by weight Tβ4 and an ophthalmically acceptable carrier, wherein the Tβ4 has a particle size of less than 10 μm.

2. The dosage of claim 1, wherein the formulation does not contain a preservative.

3. The dosage of claim 1, wherein the formulation is sterile.

4. The dosage of claim 1, wherein the formulation has a pH of 6.8-8.1.

5. The dosage of claim 1, wherein the formulation has an osmolality of approximately 280 to 350 mOsmol.

6. The dosage of claim 1, further comprising at least one tonicity agent.

7. The dosage of claim 1, further comprising sodium chloride, potassium chloride, calcium chloride, dextrose, mannitol or a combination thereof.

8. The dosage of claim 1, wherein the formulation is an aqueous solution.

9. The dosage of claim 1, wherein the formulation is a suspension.

10. The dosage of claim 1, wherein the unit dosage form is suitable for administration to a human patient.

* * * * *

SEQUENCE LISTING

<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2

```
<211> LENGTH: 6
<212> TYPE: PRT
<213> ORGANISM: Homo sapiens

<400> SEQUENCE: 2

Leu Lys Lys Thr Asn Thr
1               5

<210> SEQ ID NO 3
<211> LENGTH: 7
<212> TYPE: PRT
<213> ORGANISM: Homo sapiens

<400> SEQUENCE: 3

Lys Leu Lys Lys Thr Glu Thr
1               5

<210> SEQ ID NO 4
<211> LENGTH: 7
<212> TYPE: PRT
<213> ORGANISM: Homo sapiens

<400> SEQUENCE: 4

Leu Lys Lys Thr Glu Thr Gln
1               5
```